(12) United States Patent
Delort et al.

(10) Patent No.: US 9,109,187 B2
(45) Date of Patent: Aug. 18, 2015

(54) OUD ODORANTS

(75) Inventors: Estelle Delort, Geneva (CH); Josef Limacher, Soral (CH)

(73) Assignee: Firmenich SA, Geneva (CH)

( * ) Notice: Subject to any disclaimer, the term of this patent is extended or adjusted under 35 U.S.C. 154(b) by 57 days.

(21) Appl. No.: 14/241,444

(22) PCT Filed: Aug. 9, 2012

(86) PCT No.: PCT/EP2012/065617
§ 371 (c)(1),
(2), (4) Date: Feb. 26, 2014

(87) PCT Pub. No.: WO2013/029958
PCT Pub. Date: Mar. 7, 2013

(65) Prior Publication Data
US 2014/0371121 A1    Dec. 18, 2014

(30) Foreign Application Priority Data
Aug. 29, 2011 (EP) .................... 11179124

(51) Int. Cl.
| | | |
|---|---|---|
| *A61K 8/00* | (2006.01) | |
| *C11B 9/00* | (2006.01) | |
| *A61K 8/34* | (2006.01) | |
| *A61Q 5/02* | (2006.01) | |
| *A61Q 5/06* | (2006.01) | |
| *A61Q 15/00* | (2006.01) | |
| *A61Q 19/10* | (2006.01) | |
| *C11D 3/50* | (2006.01) | |

(52) U.S. Cl.
CPC ............... *C11B 9/0061* (2013.01); *A61K 8/347* (2013.01); *A61Q 5/02* (2013.01); *A61Q 5/06* (2013.01); *A61Q 15/00* (2013.01); *A61Q 19/10* (2013.01); *C11D 3/50* (2013.01)

(58) Field of Classification Search
CPC .............................. C07C 39/06; C11B 9/0061
See application file for complete search history.

(56) References Cited

FOREIGN PATENT DOCUMENTS

WO    WO 96/30470 A1    10/1996

OTHER PUBLICATIONS

International Search Report and Written Opinion, application PCT/EP2012/065617, mailed Sep. 26, 2012.
Czerny et al., Journal of Agricultural and Food Chemistry, vol. 57, 2009, pp. 9979-9984.
Cullere et al., Food Chem., vol. 122, 2010, pp. 300-306.

*Primary Examiner* — John Hardee
(74) *Attorney, Agent, or Firm* — Winston & Strawn LLP

(57) ABSTRACT

The present invention relates to some specific 3-(lower alkyl) phenols as key ingredients of perfuming compositions having an oud character.

13 Claims, No Drawings

OUD ODORANTS

This application is a 371 filing of International Patent Application PCT/EP2012/065617 filed Aug. 9, 2012, which claims the benefit of European application no. EP 11179124.0 filed Aug. 31, 2011.

TECHNICAL FIELD

The present invention relates to the field of perfumery. More particularly, it concerns some specific 3-(lower alkyl) phenols as key ingredients of perfuming compositions having an oud character.

PRIOR ART

Oud is a resinous heartwood native from southwest Asia and its resin is one of the world's most expensive fragrant natural resins due to the rareness of the plant and the difficulty in producing good quality resins. The odor of the oud resins is described as having a unique balsamic odor with sandalwood-ambergris tonalities.

Due to the interest for this note, the price and the limited/declining production of the natural oud resins, perfumers tend to use artificial reconstitution of the natural fragrance. However, and despite the important efforts in compounding and research of new odorants, the artificial reconstitutions developed till now lacks the truthfulness/natural aspect so typical of the genuine resin and which is the result of a unique balance and strength between the animal aspect of amber-wood tonalities and the warmness of the sandalwood tonalities.

The present invention's compounds have been described in various context of odors, in particular one may cite M. Czerny in *J. Agric. & Food Chem.*, 2009, 57, 9979 where it is mentioned that, amongst other similar phenols, 3-(n-propyl)phenol is part of the cardboard odor and has a leather-like, phenolic and ink-like odor. 3-(n-Propyl)phenol and 3-ethylphenol are also presents in the black truffle fragrance and their odors are described with similar descriptors as above (3-ethylphenol is moreover described as being truffle-like) (see L. Culleré et al. in *Food Chem.*, 2010, 122, 300). Finally the same phenols are reported as being also present in cow urine.

The document WO96/30470 discloses the use of N-ethyl-N-(3-methylphenyl)propionamide to impart oud wood odor notes. However, said document is far from suggesting the use of lower alkyl phenols according to the invention as oud odorants.

These descriptions are far away from even suggesting a possible usefulness in an oud reconstitution where odor elegance and subtlety are expected to be a prerequisite of the ingredients and the disclosures are even totally silent on any wood type of odors or effect!

DESCRIPTION OF THE INVENTION

We have now surprisingly discovered that a compound of formula

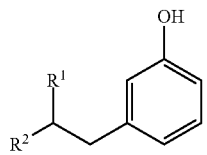

(I)

wherein $R^1$ represents a hydrogen atom or a methyl group and $R^2$ represents a hydrogen atom or a methyl or ethyl group;

can be used as perfuming ingredient, for instance to impart, improve the odor of perfuming compositions having an oud character.

According to an embodiment of the invention, $R^1$ represents a hydrogen atom or a methyl group and $R^2$ represents a hydrogen atom or a methyl group.

According to an embodiment of the invention, $R^1$ is a hydrogen atom, i.e the compound (I) is 3-(n-propyl)phenol or 3-ethylphenol or 3-(n-butyl)phenol.

According to any one of the above embodiments of the invention, $R^2$ is a methyl group. According to any one of the above embodiments of the invention, the compound of formula (I) is 3-(n-propyl)phenol.

For the sake of clarity, by the expression "perfuming composition having an oud character", or the similar, it is meant the normal meaning understood by a person skilled in the art, i.e. a perfuming composition which has an odor characterized by having at least an oud character/note/aspect, and preferably an oud odor.

Table 1 herein below shows the effect which is provided in artificial oud perfuming reconstitutions, by the invention's compounds and by similar phenols. The comparison is even more striking when considering that the odors of the phenols per se are quite similar, e.g. 3-methylphenol and 3-(n-propyl) phenol are described as having the same odor (see M. Czerny's reference cited above).

TABLE 1

Invention's compounds and their odor properties

| | Olfactive effect when added to a perfuming composition having an oud odor (artificial reconstitution)[1] |
|---|---|
| Invention's compound name | |
| 3-(n-propyl)phenol | Boosts the animal aspect and develops the warmness of the composition approaching the reconstitution fragrance to the natural resin in an unprecedented manner. Creating an exceptional synergy of the various tonalities |
| 3-ethylphenol | Boosts the animal aspect of the amberis notes while developing a warm tonality, and significantly improves the truthfulness and natural aspect of the original composition |
| 3-(i-butyl)phenol | Boosts the warm tonality and also the animal aspect. Although the effect is stronger on the warm side, the overall effect is still equilibrated and improvement of the truthfulness and natural aspect of the original composition is positive and pleasant |
| 3-(n-butyl)phenol | Boosts the warm tonality and also the animal aspect. The overall effect is slightly weaker than for the 3-(n-propyl)phenol |
| Comparative compound name | |
| 3-(i-propyl)phenol | Imparts a leather and mineral note with little interest for the oud odor and has no effect on the truthfulness and natural aspect of the original composition |

TABLE 1-continued

Invention's compounds and their odor properties

| | Olfactive effect when added to a perfuming composition having an oud odor (artificial reconstitution)[1] |
|---|---|
| 3-methylphenol | Imparts a phenolic/guaiacol note without interest for the oud odor and has no effect on the truthfulness and natural aspect of the original composition |
| 3-(n-pentyl)phenol | Imparts a phenolic/nutty note without interest for the oud odor and has no effect on the truthfulness and natural aspect of the original composition |

[1]See details of the composition in Example 1

As can be seen above, the invention's compounds have the unique capacity to act more on the initial composition fragrance by creating a synergy between the various tonalities than by imparting their specific odor properties, which in fact become quite unperceivable as such. This effect is very surprising and totally absent in other structurally similar compounds having similar odor properties per se.

As mentioned above, the invention concerns the use of a compound of formula (I) as perfuming ingredient. In other words, it concerns a method to confer, enhance, improve or modify the odor of an oud-like perfuming composition or of a perfumed article, which method comprises adding to said composition or article an effective amount of at least a compound of formula (I). By "use of a compound of formula (I)", it has to be understood here also the use of any composition containing a compound (I) and which can be advantageously employed in perfumery industry.

Said compositions, which in fact can be advantageously employed as perfuming ingredients, are also an object of the present invention.

Therefore, another object of the present invention is an oud-like perfuming composition (or a perfuming compositions having an oud character) comprising:

i) as perfuming ingredient, at least one invention's compound as defined above;
ii) a perfumery base having a oud character; and
iii) optionally at least one perfumery adjuvant.

By "perfumery carrier" we mean here a material which is practically neutral from a perfumery point of view, i.e. that does not significantly alter the organoleptic properties of perfuming ingredients. Said carrier may be a liquid or a solid.

As liquid carrier one may cite, as non-limiting examples, an emulsifying system, i.e. a solvent and a surfactant system, or a solvent commonly used in perfumery. A detailed description of the nature and type of solvents commonly used in perfumery cannot be exhaustive. However, one can cite as non-limiting examples solvents such as dipropyleneglycol, diethyl phthalate, isopropyl myristate, benzyl benzoate, 2-(2-ethoxyethoxy)-1-ethanol or ethyl citrate, which are the most commonly used. For the compositions which comprise both a perfumery carrier and a perfumery base, other suitable perfumery carriers than those previously specified, can be also ethanol, water/ethanol mixtures, limonene or other terpenes, isoparaffins such as those known under the trademark Isopar® (origin: Exxon Chemical) or glycol ethers and glycol ether esters such as those known under the trademark Dowanol® (origin: Dow Chemical Company).

As solid carrier one may cite, as non-limiting examples, absorbing gums or polymers, or yet encapsulating materials. Examples of such materials may comprise wall-forming and plasticizing materials, such as mono, di- or trisaccharides, natural or modified starches, hydrocolloids, cellulose derivatives, polyvinyl acetates, polyvinylalcohols, proteins or pectins, or yet the materials cited in reference texts such as H. Scherz, Hydrokolloide: Stabilisatoren, Dickungs- and Geliermittel in Lebensmitteln, Band 2 der Schriftenreihe Lebensmittelchemie, Lebensmittelqualität, Behr's Verlag GmbH & Co., Hamburg, 1996. The encapsulation is a well known process to a person skilled in the art, and may be performed, for instance, using techniques such as spray-drying, agglomeration or yet extrusion; or consists of a coating encapsulation, including coacervation and complex coacervation technique.

By "a perfumery base having an oud character" we mean here a composition comprising at least two perfuming co-ingredients, and which is characterized by having a fragrance comprising an odor character or even characterized by having an oud odor. A person skilled in the art, i.e. a perfumer, is perfectly able to assess if a perfumery base possesses or not such oud character.

Said perfuming co-ingredient is not of formula (I). Moreover, by "perfuming co-ingredient" it is meant here a compound which is used in a perfuming preparation or a composition to impart a hedonic effect. In other words, such a co-ingredient, to be considered as being a perfuming one, must be recognized by a person skilled in the art as being able to impart or modify in a positive or pleasant way the odor of a composition, and not just as having an odor.

The nature and type of the perfuming co-ingredients present in the base do not warrant a more detailed description here, which in any case would not be exhaustive, the skilled person being able to select them on the basis of his general knowledge and according to intended use or application and the desired organoleptic effect. In general terms, these perfuming co-ingredients belong to chemical classes as varied as alcohols, lactones, aldehydes, ketones, esters, ethers, acetates, nitriles, terpenoids, nitrogenous or sulphurous heterocyclic compounds and essential oils, and said perfuming co-ingredients can be of natural or synthetic origin. Many of these co-ingredients are in any case listed in reference texts such as the book by S. Arctander, Perfume and Flavor Chemicals, 1969, Montclair, N.J., USA, or its more recent versions, or in other works of a similar nature, as well as in the abundant patent literature in the field of perfumery. It is also understood that said co-ingredients may also be compounds known to release in a controlled manner various types of perfuming compounds.

Typical perfuming co-ingredients commonly used in perfumery base having an oud character are, as non limiting examples: castoreum, benzylacetone, pentanoic acid, 2-methoxy-4-methylphenol, 4-methylphenol, cypriol essential oil (e.g. cyperus scariosus), 2,6,6-trimethyl-1,3-cyclohexadiene-1-carbaldehyde (known also as Safranal), 2,3,3-trimethyl-1-indanone (known also as Safraleine®), (−)-(8R)-8,12-epoxy-13,14,15,16-tetranorlabdane (known also as Ambrox®), dodecahydro-3a,6,6,9a-tetramethyl-naphtho[2,1-b]furan (known also as Cetalox®), 4-(4-methoxyphenyl)-2-butanone, 3,3-dimethyl-5-(2,2,3-trimethyl-3-cyclopenten-1-yl)-4-penten-2-ol (known also as Polysantol®), 5-(2,2,3-trimethyl-3-cyclopentenyl)-3-methylpentan-2-ol (known also as Sandela®), β-santalol and/or santal oil.

According to any one of the above embodiments, said perfumery base comprises at least three or four of the perfuming co-ingredients listed above.

By "perfumery adjuvant" we mean here an ingredient capable of imparting additional added benefit such as a color, a particular light resistance, chemical stability, etc. A detailed description of the nature and type of adjuvant commonly used in perfuming bases cannot be exhaustive, but it has to be mentioned that said ingredients are well known to a person skilled in the art.

An invention's composition consisting of at least one compound of formula (I) and at least one perfumery carrier represents a particular embodiment of the invention as well as a perfuming composition comprising at least one compound of formula (I), at least one perfumery carrier, at least one perfumery base, and optionally at least one perfumery adjuvant.

It is useful to mention here that the possibility to have, in the compositions mentioned above, more than one compound of formula (I) is important as it enables the perfumer to prepare accords, perfumes, possessing various degrees of the imparted effect, creating thus new tools for his work.

Furthermore, the invention's compound can also be advantageously used in all the fields of modern perfumery, i.e. fine or functional perfumery, to positively impart or modify the odor of a consumer product into which said compound (I) is added. Consequently, a perfuming consumer product which comprises:
i) as perfuming ingredient, at least one perfuming composition according to the invention, as defined above; and
ii) a perfumery consumer base;
is also an object of the present invention.

The invention's compound can be added as such or as part of an invention's perfuming composition.

For the sake of clarity, it has to be mentioned that, by "perfuming consumer product" it is meant a consumer product which is expected to deliver at least a perfuming effect, in other words it is a perfumed consumer product. For the sake of clarity, it has to be mentioned that, by "perfumery consumer base" we mean here the functional formulation, as well as optionally additional benefit agents, corresponding to a consumer product which is compatible with perfuming ingredients and is expected to deliver a pleasant odor to the surface to which it is applied (e.g. skin, hair, textile, or home surface). In other words, a perfuming consumer product according to the invention comprises the functional formulation, as well as optionally additional benefit agents, corresponding to the desired consumer product, e.g. a detergent or an air freshener, and an olfactive effective amount of at least one invention's compound.

The nature and type of the constituents of the perfumery consumer base do not warrant a more detailed description here, which in any case would not be exhaustive, the skilled person being able to select them on the basis of his general knowledge and according to the nature and the desired effect of said product.

Non-limiting examples of suitable perfumery consumer base can be a perfume, such as a fine perfume, a cologne or an after-shave lotion; a fabric care product, such as a liquid or solid detergent, a fabric softener, a fabric refresher, an ironing water, a paper, or a bleach; a body-care product, such as a hair care product (e.g. a shampoo, a coloring preparation or a hair spray), a cosmetic preparation (e.g. a vanishing cream or a deodorant or antiperspirant), or a skin-care product (e.g. a perfumed soap, shower or bath mousse, oil or gel, or a hygiene product); an air care product, such as an air freshener or a "ready to use" powdered air freshener; or a home care product, such as a wipe, a dish detergent or hard-surface detergent.

Some of the above-mentioned consumer product bases may represent an aggressive medium for the invention's compound, so that it may be necessary to protect the latter from premature decomposition, for example by encapsulation or by chemically bounding it to another chemical which is suitable to release the invention's ingredient upon a suitable external stimulus, such as an enzyme, light, heat or a change of pH.

The proportions in which the compounds according to the invention can be incorporated into the various aforementioned articles or compositions vary within a wide range of values. These values are dependent on the nature of the article to be perfumed and on the desired organoleptic effect as well as the nature of the co-ingredients in a given base when the compounds according to the invention are mixed with perfuming co-ingredients, solvents or additives commonly used in the art.

For example, in the case of perfuming compositions, typical concentrations are in the order of 0.005% to 0.7% by weight, or even in the order of 0.015% to 0.35%, of the compounds of the invention based on the weight of the composition into which they are incorporated. Concentrations lower than these, such as in the order of 0.001% to 0.25% by weight, can be used when these compounds are incorporated into perfumed articles, percentage being relative to the weight of the article.

EXAMPLES

Example 1

Preparation of a Perfuming Composition

A perfuming composition having a woody, oud character, was prepared by admixing the following ingredients:

| Parts by weight | Ingredient |
|---|---|
| 80 | Benzylacetone |
| 20 | Cashmeran ® [1] |
| 140 | Castoreum |
| 20 | Cetalox ® [2] |
| 350 | 10%*** Civettine essential oil |
| 300 | Cypriol oil |
| 250 | (1'R,E)-2-ethyl-4-(2',2',3'-trimethyl-3'-cyclopenten-1'-yl)-2-buten-1-ol [3] |
| 50 | 2-Methyl-4-(2,2,3-trimethyl-3-cyclopenten-1-yl)-4-penten-1-ol [3] |
| 110 | Gaïac |
| 750 | 70%** Galaxolide ® [4] |
| 100 | Alpha Iso methylionone |
| 20 | Methylnaphthylcetone |
| 50 | Muscenone ™ [5] Delta |
| 20 | 10%* Myrrhone ® [6] |
| 180 | 10%* Safranal |
| 500 | Sandalwood 77125 D [7] |
| 50 | 1%* Scatol |
| 2990 | |

*in dipropyleneglycol
**in isopropyle myristate
***in tri-ethyl citrate
[1] 1,2,3,5,6,7-hexahydro-1,1,2,3,3-pentamethyl-4-indenone; origin: International Flavors & Fragrances, USA
[2] dodecahydro-3a,6,6,9a-tetramethyl-naphtho[2,1-b]furan; origin: Firmenich SA, Geneva, Switzerland
[3] origin: Firmenich SA, Geneva, Switzerland
[4] 1,3,4,6,7,8-hexahydro-4,6,6,7,8,8-hexamethyl-cyclopenta-g-2-benzopyrane; origin: International Flavors & Fragrances, USA
[5] 3-methyl-5-cyclopentadecen-1-one; origin: Firmenich SA, Geneva, Switzerland
[6] 4-(2,2,C-3,T-6-tetramethyl-R-1-cyclohexyl)-3-buten-2-one; origin: Firmenich SA, Geneva, Switzerland
[7] specialty base of the sandalwood type; origin: Firmenich SA, Geneva, Switzerland The compounds mentioned above in Table 1 were added each at 10 parts by weight to the above-described composition thus imparting to the latter the effect described in Table 1.

Example 2

Preparation of a Perfuming Composition

A perfuming composition, of the woody, musky and floral type and having an oud aspect, was prepared by admixing the following ingredients:

| Parts by weight | Ingredient |
| --- | --- |
| 10 | Isoeugenyl acetate |
| 60 | Benzyl acetate |
| 20 | 10%* Aldehyde C 11 lenique |
| 100 | Hexylcinnamic aldehyde |
| 100 | Benzyl benzoate |
| 20 | Benzophenone |
| 30 | Benzylacetone |
| 10 | Camphor |
| 20 | 8-Methoxy-2,6,6,8-tetramethyl-tricyclo[5.3.1.0(1,5)]undecane |
| 150 | Citronellol |
| 370 | Cypriol oil |
| 30 | Dimethyloctanol |
| 10 | Dorinone ® [1)] Beta |
| 10 | Eugenol |
| 40 | Exaltolide ® [2)] Total |
| 70 | Geraniol |
| 500 | Gurjun Baume |
| 150 | Helvetolide ® [3)] |
| 40 | Hydroxycitronellal |
| 150 | Iralia ® [4)] |
| 50 | Kephalis [5)] |
| 10 | 1-(2,2,3,6-Tetramethyl-cyclohexyl)-3-hexanol |
| 80 | Linalol [6)] |
| 50 | Lyral ® [7)] |
| 100 | Musc ketone |
| 50 | 10%* Nutmeg essential oil |
| 10 | Myrrhone ® [8)] |
| 350 | Hedione ® [9)] |
| 40 | Nerol |
| 120 | Patchouli oil |
| 500 | Phenethylol |
| 50 | 10%* Methyl phenylacetate |
| 30 | Phenylethyl phenylacetate |
| 10 | 9-Decen-1-ol |
| 100 | Rose essential oil |
| 40 | Acetate de 2,2,2-trichloro-1-phenylethyle [6)] |
| 80 | 10%* Safranal |
| 60 | 10%* Ethyl salicylate |
| 120 | Benzyl salicylate |
| 80 | Cis-3-Hexenol salicylate |
| 180 | Sandela ® [10)] |
| 360 | Santal esssential oil |
| 40 | Terpineol |
| 20 | 10%* Thymol |
| 40 | Tonalide ® [11)] |
| 80 | Trimofix ® [12)] |
| 10 | (2,2-Dimethoxyethyl)benzene [6)] |
| 250 | Vertofix ® [13)] Cœur |
| 100 | Vetyver oil |
| 4900 | |

*in dipropyleneglycol
[1)] 1-(2,6,6-trimethyl-1-cyclohexen-1-yl)-2-buten-1-one; origin: Firmenich SA, Geneva, Switzerland
[2)] pentadecanolide; origin: Firmenich SA, Geneva, Switzerland
[3)] (1S,1'R)-2-[1-(3',3'-dimethyl-1'-cyclohexyl)ethoxy]-2-methylpropyl propanoate; origin: Firmenich SA, Geneva, Switzerland
[4)] mixture of methylionones isomers; origin: Firmenich SA, Geneva, Switzerland
[5)] 4-(1-ethoxyethenyl)-3,3,5,5-tetramethyl-cyclohexan-1-one; origin: Givaudan SA, Vernier, Switzerland
[6)] origin: Firmenich SA, Geneva, Switzerland
[7)] 4/3-(4-hydroxy-4-methylpentyl)-3-cyclohexene-1-carbaldehyde; origin: International Flavors & Fragrances, USA
[8)] 4-(2,2,C-3,T-6-tetramethyl-R-1-cyclohexyl)-3-buten-2-one; origin: Firmenich SA, Geneva, Switzerland
[9)] methyl dihydrojasmonate; origin: Firmenich SA, Geneva, Switzerland
[10)] 5-(2,2,3-Trimethyl-3-cyclopentenyl)-3-methylpentan-2-ol; origin: Givaudan SA, Vernier, Switzerland
[11)] (5,6,7,8-Tetrahydro-3,5,5,6,8,8-hexamethyl-2-naphtyl)-1-ethanone; origin: Firmenich SA, Geneva, Switzerland
[12)] methyl 2,5,10-trimehtyl-2,5,9-cyclododecatrien-1-yl ketone & isomers; origin: International Flavors & Fragrances, USA
[13)] methyl cedryl ketone; origin: International Flavors & Fragrances, USA The addition of 100 parts by weight of a 1% w/w solution of 3-(n-propyl)phenol in dipropyleneglycol to the above-described composition transformed the original oud aspect providing a fragrance with a natural oud note, and overall the effect is similar to the oud obtained using directly the natural oud oil.

What is claimed is:

1. A method to confer, enhance, improve or modify the odor of an oud-like perfuming composition or of a perfumed article, which method comprises adding to said composition or article an effective amount of at least a compound of formula (I)

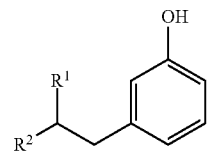

(I)

wherein $R^1$ represents a hydrogen atom or a methyl group and $R^2$ represents a hydrogen atom or a methyl or ethyl group.

2. A method according to claim 1, wherein said $R^1$ is a hydrogen atom.

3. A method according to claim 1, wherein said compound of formula (I) is 3-(n-propyl)phenol.

4. A method according to claim 1, wherein the compound is added to a perfuming composition comprising a perfumery base having an oud character; and optionally, at least one perfumery adjuvant.

5. A method according to claim 4, wherein said perfumery base comprises at least three perfuming co-ingredients selected amongst castoreum, benzylacetone, pentanoic acid, 2-methoxy-4-methylphenol, 4-methylphenol, cypriol essential oil, 2,6,6-trimethyl-1,3-cyclohexadiene-1-carb aldehyde, 2,3,3-trimethyl-1-indanone, (−)-(8R)-8,12-epoxy-13,14,15,16-tetranorlabdane, dodecahydro-3a,6,6,9a-tetramethyl-naphtho[2,1-b]furan, 4-(4-methoxyphenyl)-2-butanone, 3,3-dimethyl-5-(2,2,3-trimethyl-3-cyclopenten-1-yl)-4-penten-2-ol, 5-(2,2,3-trimethyl-3-cyclopentenyl)-3-methylpentan-2-ol, β-santalol and/or santal oil.

6. A method according to claim 1, wherein the compound is added to a perfuming consumer product comprising a perfumery base having an oud character; a perfumery consumer base and, optionally, at least one perfumery adjuvant.

7. A method according to claim 6, wherein said perfumery consumer base is a perfume, a fabric care product, a body-care product, an air care product or a home care product.

8. A method according to claim 6, wherein said perfumery consumer base is a fine perfume, a cologne, an after-shave lotion, a liquid or solid detergent, a fabric softener, a fabric refresher, an ironing water, a paper, a bleach, a shampoo, a coloring preparation, a hair spray, a vanishing cream, a deodorant or antiperspirant, a perfumed soap, shower or bath mousse, oil or gel, a hygiene product, an air freshener, a "ready to use" powdered air freshener, a wipe, a dish detergent or hard-surface detergent.

9. A perfuming composition having an oud character comprising:
i) as perfuming ingredient, at least one compound of formula

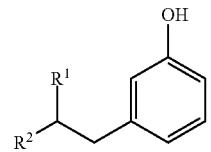

(I)

wherein $R^1$ represents a hydrogen atom or a methyl group and $R^2$ represents a hydrogen atom or a methyl or ethyl group;
ii) a perfumery base having an oud character; and
iii) optionally at least one perfumery adjuvant.

10. A perfuming composition according to claim 9, wherein said perfumery base comprises at least three perfuming co-ingredients selected amongst castoreum, benzylacetone, pentanoic acid, 2-methoxy-4-methylphenol, 4-methylphenol, cypriol essential oil, 2,6,6-trimethyl-1,3-cyclohexadiene-1-carbaldehyde, 2,3,3-trimethyl-1-indanone, (−)-(8R)-8,12-epoxy-13,14,15,16-tetranorlabdane, dodecahydro-3a,6,6,9a-tetramethyl-naphtho[2,1-b]furan, 4-(4-methoxyphenyl)-2-butanone, 3,3-dimethyl-5-(2,2,3-trimethyl-3-cyclopenten-1-yl)-4-penten-2-ol, 5-(2,2,3-trimethyl-3-cyclopentenyl)-3-methylpentan-2-ol, β-santalol and/or santal oil.

11. A perfuming consumer product comprising:
i) at least one perfuming composition comprising
a) as perfuming ingredient, at least one compound of formula (I)

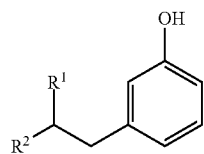
(I)

wherein $R^1$ represents a hydrogen atom or a methyl group and $R^2$ represents a hydrogen atom or a methyl or ethyl group;
b) a perfumery base having an oud character; and
c) optionally at least one perfumery adjuvant;
ii) a perfumery consumer base.

12. A perfuming consumer product according to claim 11, wherein said perfumery consumer base is a perfume, a fabric care product, a body-care product, an air care product or a home care product.

13. A perfuming consumer product according to claim 11, wherein said perfumery consumer base is a fine perfume, a cologne, an after-shave lotion, a liquid or solid detergent, a fabric softener, a fabric refresher, an ironing water, a paper, a bleach, a shampoo, a coloring preparation, a hair spray, a vanishing cream, a deodorant or antiperspirant, a perfumed soap, shower or bath mousse, oil or gel, a hygiene product, an air freshener, a "ready to use" powdered air freshener, a wipe, a dish detergent or hard-surface detergent.

* * * * *